United States Patent [19]

Zarrin et al.

[11] Patent Number: 5,076,097

[45] Date of Patent: Dec. 31, 1991

[54] METHOD AND APPARATUS FOR DETERMINING CONCENTRATION OF MACROMOLECULES AND COLLOIDS IN A LIQUID SAMPLE

[75] Inventors: Fahimeh Zarrin, St. Paul; Stanley L. Kaufman, Minneapolis; Frank D. Dorman, Golden Valley, all of Minn.

[73] Assignee: TSI Incorporated, St. Paul, Minn.

[21] Appl. No.: 546,004

[22] Filed: Jun. 28, 1990

[51] Int. Cl.$^5$ .................................................. G01N 30/02
[52] U.S. Cl. ........................................ 73/61.1 C; 73/53
[58] Field of Search ...................... 73/53, 61 R, 61.1 C

[56] References Cited

U.S. PATENT DOCUMENTS

| | | | |
|---|---|---|---|
| 2,774,652 | 12/1956 | Vonnegut . | |
| 2,897,059 | 7/1959 | VanLuik, Jr. . | |
| 3,094,392 | 6/1963 | Skala . | |
| 3,102,192 | 8/1963 | Skala . | |
| 3,117,841 | 1/1964 | VanLuik, Jr. . | |
| 3,410,663 | 11/1968 | Reilly et al. . | |
| 3,522,431 | 8/1970 | Coffey et al. | 250/43.5 |
| 3,562,128 | 2/1971 | Coffey | 204/193 |
| 3,607,085 | 9/1971 | Fusco | 23/232 R |
| 3,674,435 | 7/1972 | VanLuik, Jr. et al. | 23/232 R |
| 3,711,248 | 1/1973 | Coffey | 23/232 R |
| 3,827,555 | 8/1974 | Kamentsky et al. | 209/111.7 |
| 3,937,662 | 2/1976 | Bartik | 210/23 |
| 3,996,004 | 12/1976 | Fine et al. | 23/230 PC |
| 4,238,194 | 12/1980 | Dunham | 23/230 R |
| 4,403,147 | 9/1983 | Melera et al. | 73/61.1 C X |
| 4,699,718 | 10/1987 | Jones et al. | 210/659 |
| 4,761,074 | 8/1988 | Kohsaka et al. | 356/37 |
| 4,794,086 | 12/1988 | Kasper et al. | 436/36 |

FOREIGN PATENT DOCUMENTS 3516188 11/1986 Fed. Rep. of Germany ..... 73/23.35

OTHER PUBLICATIONS

"Recent Developments in Analytical Chromatography," Milos V. Novotny, *Science*, Articles, vol. 246, pp. 51–57, Oct. 6, 1989.
"Subattomole Amino Acid Analysis by Capillary Zone Electrophoresis and Laser-Induced Fluorescence," Yung-Fong Cheng, Norman J. Dovichi, *Science*, Reports, vol. 242, pp. 562–564, Oct. 28, 1988.
"The Brave New World of Flow Cytometry," *Laser and Applications*, Biomedical News, p. 40, Aug. 1985.
"Electrospray Ionization for Mass Spectrometry of Large Biomolecules," John B. Fenn, Matthias Mann, Chin Kai Meng, Shek Fu Wong, Craig M. Whitehouse, *Science*, Articles, vol. 246, pp. 64–71, Oct. 6, 1989.
"Detectors for Liquid Chromatography," Edward S. Yeung, Robert E. Synovec, *Analytical Chemistry*, vol. 58, No. 12, pp. 1237A–1256A, Oct. 1986.
"A Condensation Nucleus Counter Designed for Ultrafine Particle Detection Above 3nm Diameter," Patricia B. Keady, Veryl L. Denler, Gilmore J. Sem, Mark R. Stolzenburg, Peter H. McMurry, presented at the 12th International Conference on Atmospheric Aerosols and Nucleation, Vienna, Austria, Aug. 22–27, 1988.
TSI Model 3075/3076 Constant Output Atomizer Instruction Manual, TSI Incorporated.
Condensation Particle Counter, TSI Model 3022, TSI Incorporated.
"Study of the Qualitative and Quantitative Properties of the Light-Scattering Detector," Andrzej Stolyhwo, Henry Colin, Michel Martin, Georges Guiochon, *Journal of Chromatography*, 288 (1984), pp. 253–255.
Exhibit A—Abstracts from U.S. Pat. Nos. 4,542,293, 4,531,056, 4,214,160 and 4,075,479.

*Primary Examiner*—Hezron E. Williams
*Assistant Examiner*—Joseph W. Roskos
*Attorney, Agent, or Firm*—Merchant, Gould, Smith, Edell, Welter & Schmidt

[57] ABSTRACT

An apparatus and method for determining the concentration of macromolecules and colloids in a liquid sample is disclosed. The apparatus preferably includes an electrospray apparatus 16 for forming droplets from the sample. Liquid is removed from the droplets by drying in the electrospray apparatus 16, thereby forming an aerosol. The aerosol of a size greater than a predetermined size is then counted by a condensation nucleus counter 52. In this manner, the target macromolecules and colloids are counted. This apparatus is capable of detecting very small macromolecules and colloids of a wide range of materials in a liquid, for example, individual molecules having molecular weight as small as 10,000.

22 Claims, 5 Drawing Sheets

METHOD AND APPARATUS FOR DETERMINING CONCENTRATION OF MACROMOLECULES AND COLLOIDS IN A LIQUID SAMPLE

FIELD OF THE INVENTION

This invention is an improved apparatus for measuring the concentration of macromolecules and colloids in a liquid sample. More particularly, this invention permits the detection of very small size macromolecules and colloids of a wide range of materials in a liquid. For example, individual molecules having molecular weight as small as 10,000 can be detected.

BACKGROUND OF THE INVENTION

Detection of low concentration samples is of interest in many fields. Currently, much effort has been devoted to developing techniques to be able to separate a sample into its components, e.g., capillary zone electrophoresis (CZE), liquid chromatography (LC), and super critical fluid chromatography (SFC). These techniques are able to resolve a minute sample into individual components. There is a need for a very sensitive detector to measure the concentration of these microscopic quantities in samples. In the above techniques, CZE, LC, SFC, and other techniques such as flow cytometry, it is desirable to have detectors which are extremely sensitive but which are also universal in the sense that they can respond to a wide variety of materials. The detector must respond to changes in some characteristic, e.g., optical property, conductivity, etc., of the sample for concentration measurement.

Numerous techniques and apparatus, such as UV and visible photometers, mass spectrometry, refractive index, fluorescence and others, have been used to detect concentrations of materials in fluid samples. However, some of these techniques which are extremely sensitive are not universal, and some which are universal are not very sensitive. Also, some detectors require a large amount of sample in order to be able to respond. Some of the presently available detectors may not function well where a large background is present or the time response of the detector may not be compatible with the sample. Further, some of the techniques are cost prohibitive and complex.

The mass spectrometer is one of the few detectors which has both very high sensitivity and a kind of universality. However, the cost is often prohibitive for many users and, therefore, an alternative must be sought. The use of mass spectrometry also requires the transfer of material to a high vacuum chamber. The requirement for a high vacuum chamber further increases the cost and complications for the user.

As mentioned, it is desirable to have a highly sensitive detector for use with various separation techniques. There are several kinds of separation techniques, including gas and liquid chromatography. All of the chromatography techniques require the use of a detection system to aid the scientist. As an example, liquid chromatography allows separation of an injected material or solute according to size or chemical properties. The solute is injected into a suitable solvent or liquid. The individual chemical compounds originally present in a mixture are resolved from each other by the selective process of distribution between two heterogeneous phases. The separation occurs between two phases known as the stationary phase and the mobile phase. The stationary phase is a dispersed medium through which the mobile phase is allowed to flow. The greater the attraction of a particular chemical compound for the stationary phase, the longer it will be retained in the system. This retention provides separation. All types of chromatography may be defined as separation processes where components are selectively retained by a stationary phase. The components are retained to different degrees and, therefore, samples may be separated based on different physical characteristics. Another separation technique which is currently used is capillary zone electrophoresis. Electrophoresis involves migration of macromolecules or colloids in a liquid due to the effect of potential difference across immersed electrodes. The molecules or colloids migrate at different rates to provide discrete zones. The molecules or colloids travel from the inlet of a capillary to the output, where they are detected as they approach the exit.

Yet another example of a technique which is benefited by a sensitive detector is flow cytometry. A flow cytometer is an apparatus which sorts cells or particles. The cells or particles are passed in a single line through a laser beam which causes them to fluoresce. Sensors then measure physical or chemical characteristics of the cells or particles. More particularly, a user may wish to utilize a flow cytometer to count cells in liquid suspension or cells in aerosols.

A detector having the ultimate sensitivity would respond to a single molecule. A universal detector which responds to single molecules still requires some means to discriminate between molecules of the solute and molecules of the solvent. The present invention addresses the problems associated with measuring concentration of macromolecules and colloids in liquid samples. The apparatus of the present invention operates in an accurate, controlled, more sensitive and universal manner. The apparatus is a real time system which possesses the sensitivity and ability to detect single molecules.

SUMMARY OF THE INVENTION

The present invention provides an apparatus for measuring concentrations of material. A preferred embodiment constructed according to the principles of the present invention is especially suited for measurements of low concentrations of samples, as utilized with a liquid chromatography system.

In the preferred embodiment of a detector apparatus constructed according to the principles of this invention, a device is utilized to form droplets from a sample. The droplets include macromolecules or colloids to be measured plus solvent and impurities. A means for removing solvent from the droplets is utilized downstream from the droplet forming means, thereby forming an aerosol. A means for selecting the particles of a size greater than a predetermined size is placed in communication with the apparatus downstream of the solvent removing means to ensure measurement of only those molecules and colloids which are of interest. Macromolecules and colloids are grown to a larger size in the preferred embodiment and aerosols less than a predetermined size are not selected due to the threshold of the counting device. This selection rejects aerosols which result from dissolved an insoluble impurities in the solvent and the sample. In this manner, the residue and particles with size smaller than predetermined size are ignored, counting only the macromolecules and colloids which the user desires to measure. The aerosols are counted by a counter, thereby providing a real time system of high sensitivity for determining concentration of macromolecules and colloids.

Therefore, according to one aspect of the invention, there is a device for determining the concentration of macromolecules and colloids in a liquid of the type that can include the macromolecules, colloids, and impurities, said device comprising means for forming droplets from the liquid; means, cooperatively connected to said droplet forming means, for removing the liquid from the droplets wherein an aerosol results; means, cooperatively connected to said liquid removing means, for selecting aerosol particles of a size greater than a predetermined size; and means for counting the aerosol particles greater than the predetermined size.

One feature of the present invention is the recognition of the need to measure single molecules. The apparatus possesses the highest sensitivity in that it is able to measure single macromolecules. The limitation on the measurement of single macromolecules is determined by the size threshold of the measuring device or condensation nucleus counter and by the nonvolatile components of the liquid which have a small molecular weight. The size threshold for response of this detector is determined by the degree of supersaturation and other parameters known and described in the literature. A single molecule of approximate size 10,000 molecular weight can be detected at the present technology by running the apparatus at specific parameters.

Another advantage of the present invention is that the threshold of the counter or condensation nucleus counter does not depend significantly on the composition of the particles. As stated earlier, most detection systems have limitations as to certain particles or materials which the system will detect. The use of a condensation nucleus counter allows the system to be virtually independent of composition of material. This universality aspect of the invention allows for accurate and efficient detection in diverse analysis of materials. Further, the invention may include use of diffusion screens to impose a lower size cut-off to remove aerosols smaller than target size; this alters the threshold which reduces the background count and improves signal-to-noise ratio. Therefore, the system is limited only by the size of the molecules. To be able to detect small macromolecules and colloids, e.g., 3 nm in diameter, which is approximately the size of an organic molecule of molecular weight 10,000, and to be virtually independent of composition of material allows measurement where it has not been feasible in the past. For example, methods such as UV absorption and fluorescence require the molecules to have very specific spectroscopic properties. This universality aspect of the invention allows for accurate and efficient detection in diverse analysis of materials.

Another advantage of the invention is that the method and apparatus for detecting concentrations of materials is able to reject matter and signals from the solvent background. In most cases of liquid chromatography, there is virtually no distinguishable difference between solvent and solutes. Therefore, most detectors respond to the background of the sample and accurate measurement of very low concentration sample is impossible. The present invention recognizes that it is advantageous to reject the residue and signals of the solvent as, for example, in use with liquid chromatography. Further, if gradient liquid chromatography methods are utilized where the solvent composition changes, the apparatus of the present invention still allows for rejection of the solvent background. In this manner, the present invention delivers more accurate data and because the sensitivity of the present invention is increased over conventional methods, lower concentrations of particles may be measured.

Yet another advantage of the invention is that the sample size needed for accurate measurements may be quite small. Analysis of amino acids in conjunction with capillary zone electrophoresis is an example of analysis where very minute samples are available. Because the invention allows detection of individual molecules, the sample size may be quite minimal. The sample volume required is limited only by the efficiency of the process of forming droplets and sampling the sample. Unlike techniques such as mass spectrometry, there is no need to transfer the material to be tested into a high vacuum chamber. The simplicity and accuracy of the present invention allow for a low cost system with high sensitivity. Further, the apparatus can be made very small, thus allowing for a field portable unit, if desired. There are no large apparatus such as large lasers or high vacuum chambers as in other methods of detection.

A further advantage of the present invention is the capability to measure the concentration of material in a real time manner. The present invention recognizes that it is highly desirable to make the measurements on-line. This on-line or real time measurement allows for continuous measurement of the sample for quick and accurate results which are necessary in chemical analysis situations. The measurements are taken in a manner which is more compatible with chromatography techniques.

Still another feature of the apparatus is the broad rang of methods and analysis which may employ the detector. For example, the detector of the present invention may be used in the areas of forensics medicine, petroleum processing, pharmaceuticals, polymers, paint manufacture, biotechnology, dyes, biology, genetics, plastics, polysaccharides, and environmental sciences, among others.

These and other advantages and features which characterize the present invention are pointed out with particularity in the claims annexed hereto and forming a further part thereof. However, for a better understanding of the invention, its advantages and objects obtained by its use, reference should be made to the drawings which form a further part hereof, and to the accompanying descriptive matter, in which there is illustrated and described a preferred embodiment of the present invention.

DESCRIPTION OF THE DRAWINGS

In the drawings, wherein like reference numerals represent like parts throughout the several views.

DETAILED DESCRIPTION OF THE PREFERRED EMBODIMENT

The present invention includes a detector for measuring the concentration of macromolecules and colloids. The invention may be utilized with chromatography and other related separation techniques. The invention is able to respond to single molecules of a size greater than a threshold size needed for nucleation.

The principles of this invention apply particularly well to its application in chemical analysis used in conjunction with a liquid chromatography apparatus. Although the invention is described in conjunction with liquid chromatography, such application is typical of only one of many applications in which the principles of the invention can be employed. For example, the present invention may be employed to measure concentration in conjunction with flow cytometry, capillary zone electrophoresis, super critical fluid chromatography, or other analytical techniques.

In a preferred embodiment, the sample to be analyzed is transferred from the outlet of a separation medium to the portion of the system to measure the concentration of target analyte where the sample is formed into droplets. The droplets are then dried in a drying column to form aerosol. This aerosol is then sampled and the target aerosols are counted by a condensation nucleus counter (CNC). The operation of CNC devices is well known in the art, and so will not be discussed in great detail here.

The CNC utilizes the aerosols where the aerosols serve as nuclei for condensation of liquid droplets from supersaturated vapor. The size threshold for response to this detector is determined by the degree of supersaturation and other known parameters. Basically, the macromolecules and colloids are increased in size by condensation so the particles are large enough to be counted by a conventional optical particle counter. The counter responds to macromolecules and colloids the size of which exceeds a threshold size needed for nucleation. Because the dissolved impurities in the sample are generally much smaller than this threshold, there is discrimination between macromolecules or colloids and dissolved impurities. Thus, the threshold of the CNC determines or selects the target particles for counting.

The CNC comprises a laser light source and focusing lenses. The particles confront or intersect the laser light thereby scattering the laser light. Collecting lenses collect the light at a photoelectric transducer which converts the light intensity to an electrical signal. The signals from the photoelectric transducer are counted and the data is transferred to a signal processor designed to deliver the desired information.

Figure 1:
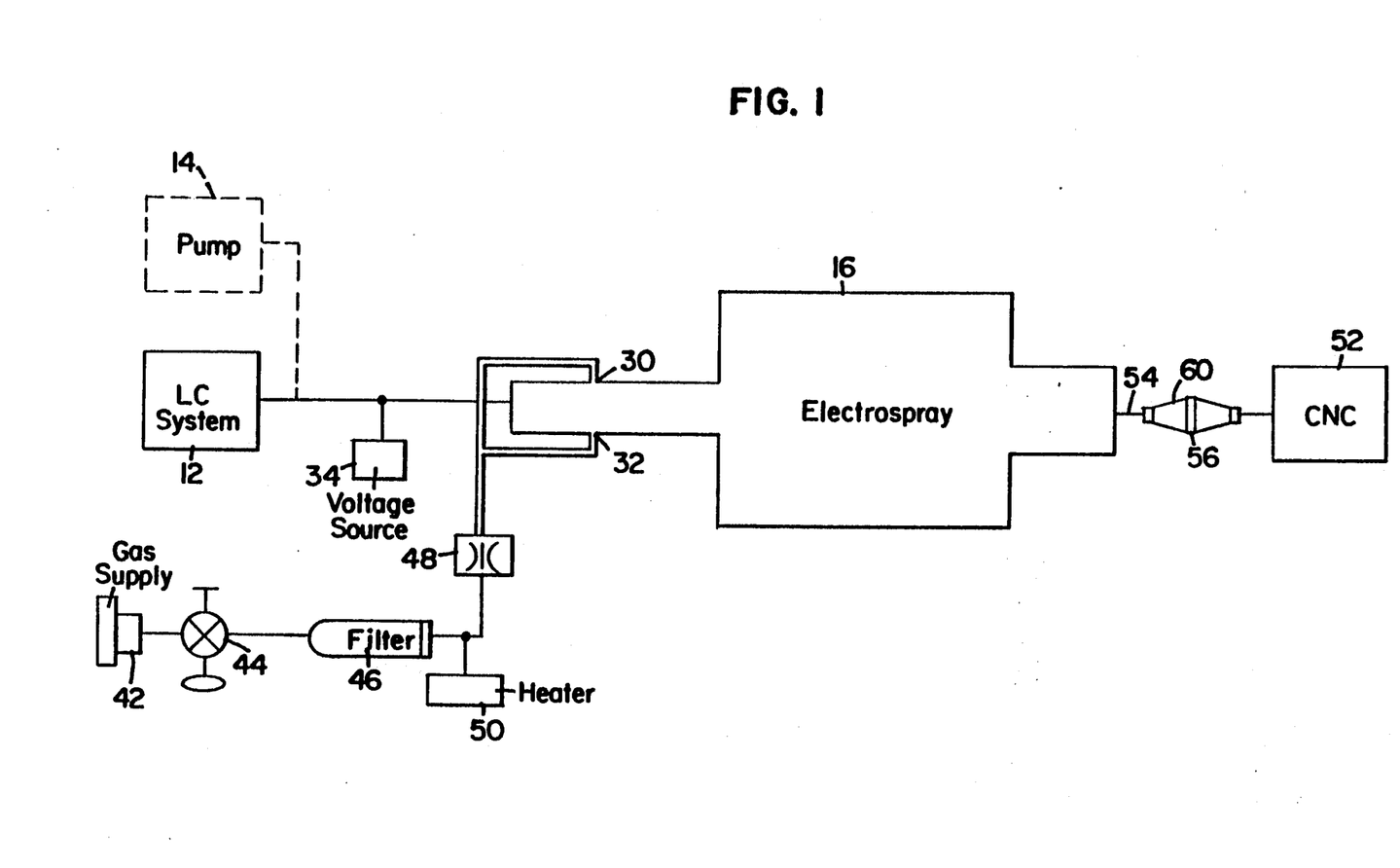
FIG. 1 is a diagrammatic illustration of the apparatus for measuring concentrations of macromolecules and colloids in a liquid sample according to the principles of the invention, utilizing an electrospray atomizer.

Referring to the drawings, a possible configuration of an apparatus 10 for detecting particles in fluid samples is shown in FIG. 1. A liquid chromatography system 12 is utilized in the preferred embodiment to supply a separated sample or analyte. The sample is separated based on a predetermined characteristic by the chromatograph and subsequently forwarded to the counter. It should be understood that any means to supply a sample is within the broad scope of this invention. The sample or analyte may also be provided, or fed, to the apparatus of the present invention by means of a syringe pump 14 as shown in FIG. 1. The syringe pump 14 feeds the sample at a selected rate and is independent of pressure downstream. In an embodiment utilizing a pump, a syringe pump having the designation Model No. 975 manufactured by Harvard Apparatus Co. is utilized. As those skilled in the art will recognize, it should be understood that any suitable conventional fittings and connectors may be utilized to introduce the analyte so as to allow the invention to operate within its broad principles. However, it should be kept in mind that materials should be utilized which do not contaminate the sample to be analyzed. In the preferred embodiment, stainless steel is utilized to provide a non-contaminating apparatus.

Figure 2:
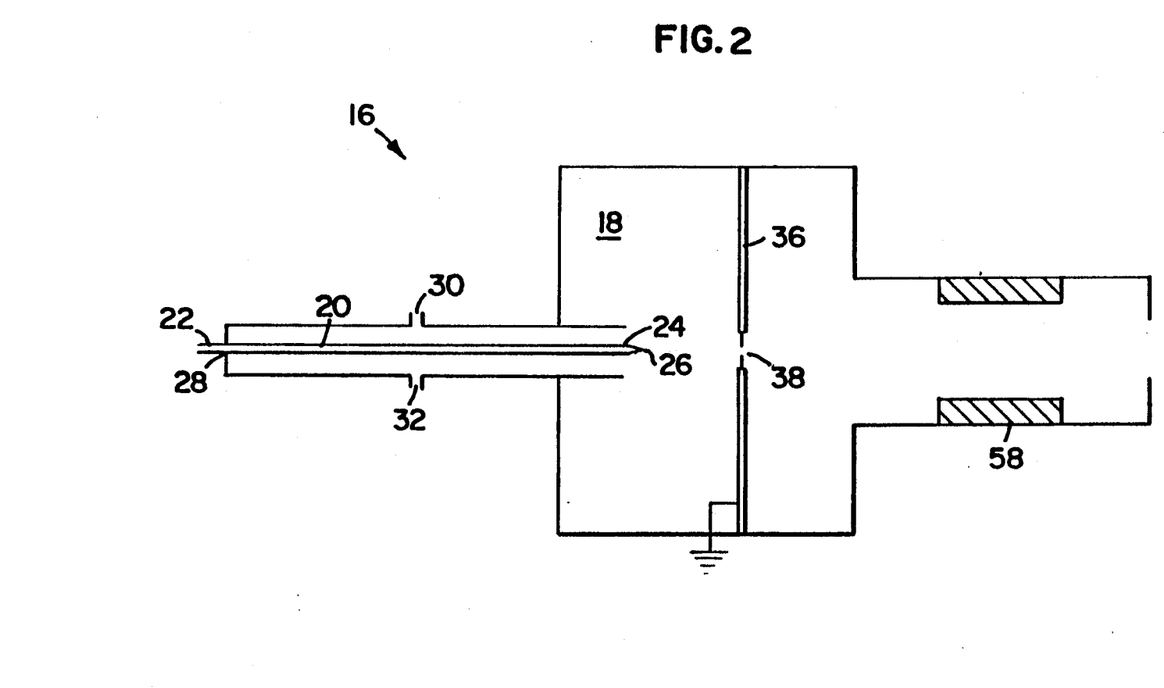
FIG. 2 is a diagrammatic illustration of the electrospray atomizer of the apparatus of FIG. 1.
Figure 3:
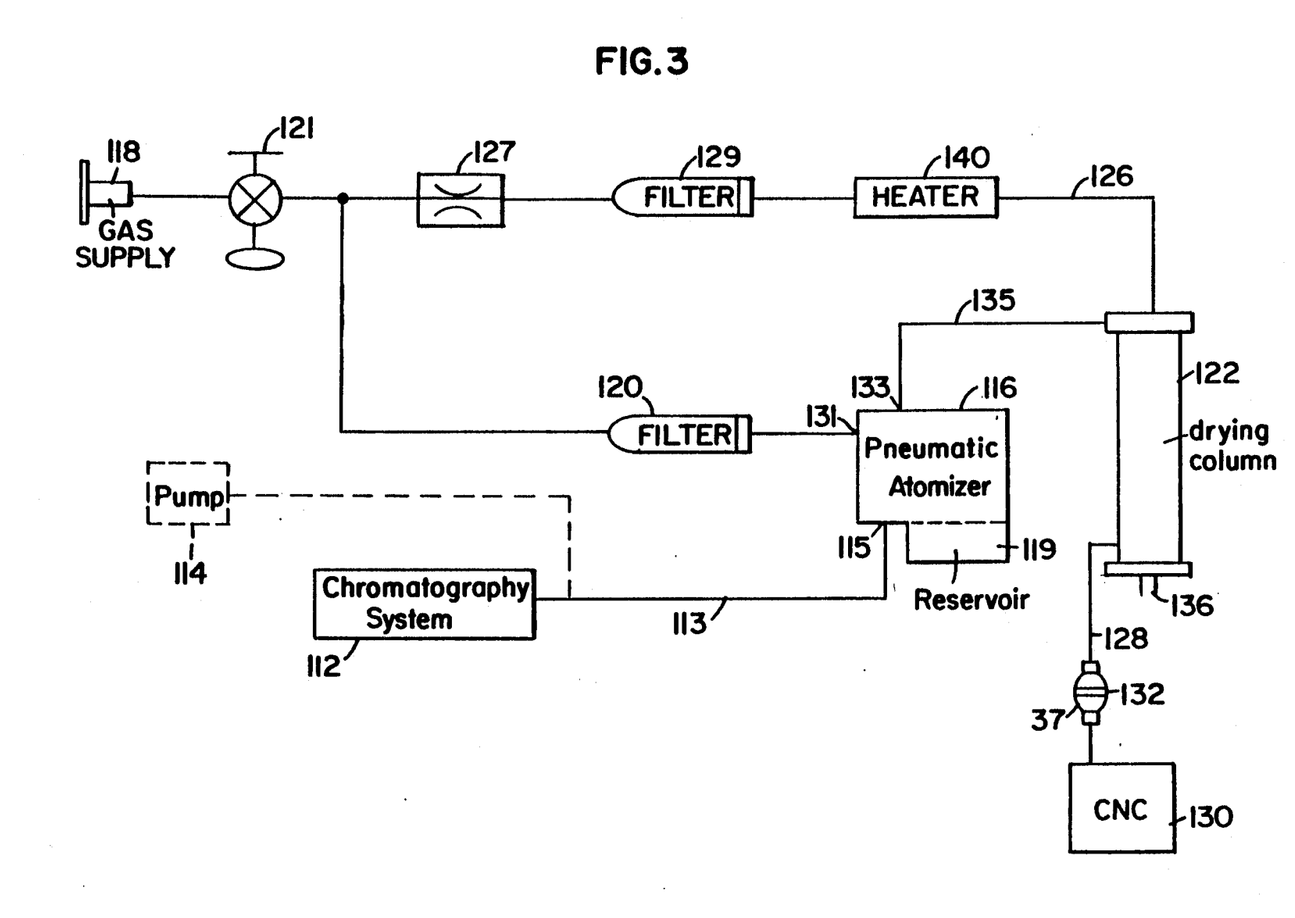
FIG. 3 is an alternative embodiment of the invention of FIG. 1 utilizing a pneumatic atomizer apparatus.
Figure 4:
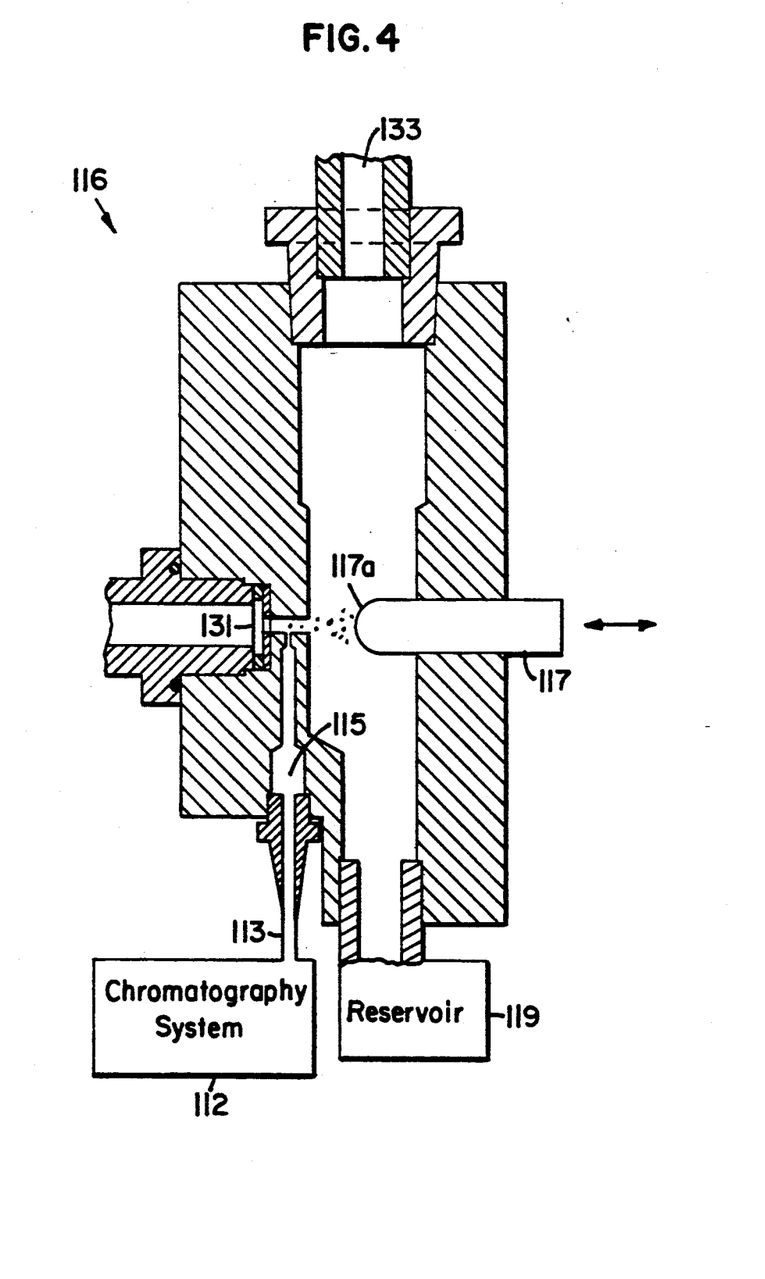
FIG. 4 is a diagrammatic illustration of the pneumatic atomizer of the apparatus of FIG. 3.

Referring to FIGS. 1 and 2, apparatus 10 is shown utilizing an electrospray apparatus 16. The electrospray apparatus 16 includes an electrospray chamber 18. Further, a needle or tube 20, having a first end 22 and a second end 24, is cooperatively connected to the outlet of the chromatography system 12 at its first end 22, while the second end 24 is located within the electrospray chamber 18. The sample or analyte passes through the chromatography apparatus 12 to the tube 20 in the preferred embodiment. The tube or needle 20 is a stainless steel capillary tube having an inner diameter of .007 inches. Further, the tube 20 is chamfered at end 24 located in the electrospray chamber 18. This chamfered end 24 forms a sharp edged conical tip 26. The tube 20 is fit into the chamber 18 through an orifice 28. The capillary tube 20 is axially aligned within the orifice 28 in the preferred embodiment.

As shown in FIGS. 1 and 2, chamber 18 includes inlets 30 and 32. Heated filtered air enters the chamber 18 at inlets 30 and 32 and is forced toward the tip 26 of tube 20. The movement of the air forces the sample to move through the chamber 18. Heater 50 is operatively connected to the apparatus downstream of air supply 42. The heated filtered air aids in the removal of the solvent from the droplets, thereby forming an aerosol. Gas supply 42, as shown in FIG. 1, is cooperatively connected to the electrospray apparatus 16. Pressure regulator 44, located upstream of the chamber 18 controls the gas supply. A filter 46 is connected to the gas supply 42 in the preferred embodiment to ensure no contaminants are introduced into the chamber 18. In the preferred embodiment, the filter is a pleated glass fiber, high efficiency filter sold by TSI Incorporated of St. Paul, Minn., known as Model No. 3074. A fixed orifice 48 is located downstream of the filter 46 to further control the flow of air. The orifice is a critical type orifice so that flow control is achieved without further regulating means.

Still referring to FIGS. 1 and 2, the chamber 18 further includes an end wall 36 having an aperture 38. The end wall 36 is positioned downstream from the chamfered tip 26 of the tube 20 so that the tube 20 is axially aligned with the axis of the aperture 36. In the preferred embodiment, the orifice or aperture 38 is 0.177 inches in diameter and the tip 26 of tube 20 is placed approximately 0.007 inches from the wall 36. The end wall 36 is connected to a ground or reference potential and is generally circular to fit within the generally cylindrical electrospray apparatus 16.

A voltage source 34 is operatively connected to the capillary tube 20. A high potential difference is generated between the capillary tube 20 and the end wall 36, which causes the liquid to electrospray thereby forming charged droplets. Those skilled in the art will recognize that proper ground, bias and insulators are utilized with the spray forming means. In the preferred embodiment, the tube 20 is maintained at 2 to 10 kilovolts relative to the walls of the chamber 18 and the surrounding cylindrical electrode. By this means, an electric field results at the needle tip 26 and charges the surface of the emerging liquid or sample. The sample is dispersed by coulomb forces into a fine spray of charged droplets. Due to generation of the electric field, the droplets migrate toward the orifice. The air, which enters at inlets 30 and 32, helps the evaporation of solvent from each droplet, decreasing its diameter as it moves toward the orifice 38. The charge density on the surface of the droplets increases until the Raleigh limit is reached, at which point the Coulomb repulsion becomes of the same order as the surface tension, resulting in instability which tears the droplet apart. Charged droplets are produced by this electrospray ionization technique.

Because the droplets are charged, they would stick or cling to the sides of the chamber or entrance to the counter and distort the results unless neutralized. Therefore, means are included in the preferred embodiment to neutralize the charge on the particles. In the preferred embodiment, an alpha source 58 is utilized to neutralize the particles. Polonium strips are used as an alpha source in the preferred embodiment, although it should be understood that any other source which will neutralize the particles may be suitable. For example, any source of ionization radiation may be used, such as a beta, gamma, x-ray or ultraviolet source.

Still referring to FIG. 1, a CNC 52, the operating principles of which have been described above, is connected to the chamber 18 by stainless steel tubing 54 to allow molecules and aerosols to pass to the CNC 52 to be counted.

One or more diffusion screens 56 may be utilized with the preferred embodiment to filter (or to collect) smaller particle sizes in order to shift the detection efficiency curve of the CNC 52 to generally larger size particles. Therefore, utilization of diffusion screens 56 allows for a change in the detection sensitivity of CNC 52. The screens 56 are placed upstream from the CNC 52, as shown in the preferred embodiment in FIG. 1. Screens 56 are arranged and configured so that the ultrafine aerosols are impacted onto screen 56 by forces of Brownian motion. Aerosols larger than a specified size are sufficiently unaffected by Brownian motion and thereby pass through the diffusion screens 56 to the CNC device 52, while smaller aerosols are captured by the screen 52. By this means, the operating range of the detector can be extended.

A diffusion filter housing 60 is utilized with the diffusion screens 56 and is cooperatively connected to tube 54. The housing 60 can contain several diffusion screens 56. The filters or screens 56 are made of stainless steel in the preferred embodiment and are of a fine mesh design. By varying the number of screens 56, it is possible to selectively remove particles less than a prescribed size. Only one or two screens 56 are required to provide the preferred apparatus 10 with a wide operating range.

In operation, a sample analyte passes through chromatograph 12 to the electrospray 16 where droplets are formed (as described above). The droplets contain macromolecules or colloids to be measured, solvent, and impurities. As one skilled in the art will recognize, the impurities can include, but are not limited to, dissolved impurities, nonvolatile residue, and contaminating solid particles. The resulting droplets are dried in electrospray chamber 18, thereby forming an aerosol. These aerosols then flow downstream toward the CNC 52.

The dried aerosol comprises: (a) the nonvolatile residue from droplets which contained dissolved impurities, but do not contain any of the macromolecules or colloids; (b) isolated macromolecules or colloids together with nonvolatile residue, resulting from droplets which contained a single macromolecule or colloid; (c) clusters of macromolecules or colloids together with nonvolatile residue, resulting from droplets which contained more than one macromolecule or colloid; (d) contaminating solid particles, either from the liquid or from the gas inlet to the atomizer, droplet generator.

The size threshold is made larger than the type (a) residue particles, so that the CNC 52 responds only to categories (b), (c), and (d). In this way, counting of single molecules is achieved. The size of type (a) particles is determined by the concentration of dissolved impurities and the initial droplet size before drying. A criterion for the successful operation of the apparatus is that the size of type (b) particles must be larger on average than that of type (a) particles.

The number of droplets forming type (c) aerosol, relative to the number forming type (b), may be estimated by a Poisson distribution (described below) whose parameter is the product of the concentration of the molecules of solute and the volume of the initial droplets formed in the atomizer. To make the number of type (c) (doublets, triplets, etc.) neglible, it suffices to make this product much less than unity, (see Appendix A). Type (d) particles depend on the existence of insoluble impurities in the solvent. Where possible, these impurities should be removed from the liquid and gas inputs to the apparatus 10.

The particles or aerosol are first enlarged by a condensing vapor to form easily detected droplets. When the vapor surrounding the particles reaches a certain degree of supersaturation, vapor begins to condense onto the aerosols with predetermined size. Degree of supersaturation is measured by the saturation ratio which is defined as the actual vapor partial pressure divided by saturation vapor pressure for a given temperature. For a given saturation ratio, the vapor can condense onto particles only if they are large enough. The lower size sensitivity of the CNC 52 is therefore determined by the operating saturation ratio.

After the aerosols are drawn into the CNC 52 and enlarged by condensation of the supersaturated vapor into droplets that measure several micrometers in diameter, the droplets pass through a lighted viewing column where they scatter light. Scattered light pulses are collected by a photodetector and converted into electrical pulses. Electrical pulses are then counted and their rate is a measure of particle concentration.

Figure 5:
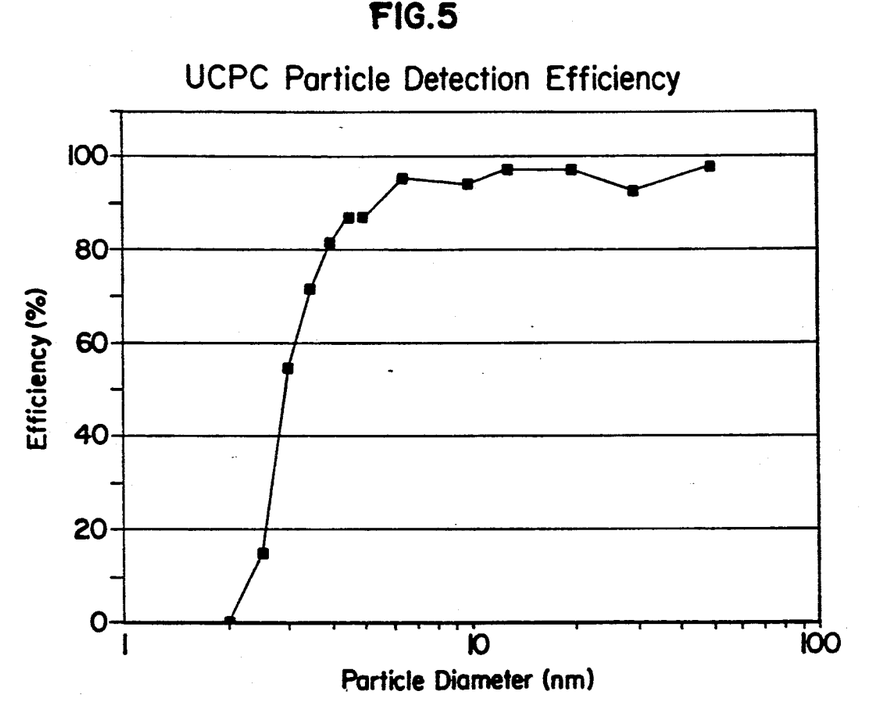
FIG. 5 is a graph illustrating the detection efficiency of a condensation nucleus counter.

FIG. 5 shows the detection efficiency of the CNC, TSI Model 3025. This figure is obtained by operating the CNC at specific parameters, e.g., using n-butyl alcohol as a condensing fluid and running the temperature of the saturator and condenser at 35° C. and 10° C. respectively. The data indicates aerosols as small as approximately 2.5 nm in diameter are counted with an efficiency of about 40%. As it is shown in FIG. 5, the counting efficiency of the detector increases as the diameter of the aerosols increases, e.g., collection efficiency is 60% for 3 nm diameter aerosols and it approaches 100% for aerosols larger than 10 nm in diameter. This range of particle detection, 2 nm to 100 nm, very well matches the range of a wide variety of macromolecules and colloids, which are of interest in many areas of science.

The present invention allows for counting of macromolecules and colloids and discriminates against the nonvolatile residue. The device discriminates between the types of aerosol because the size of the macromolecules and colloids exceeds the size of the nonvolatile residue. Therefore, only residue particles are eliminated from the count or measurement of concentration. The contaminating solid particles which may be formed from the aerosol are solely dependent on the existence of impurities in the solvent or impurities introduced from the gas inputs to the detector. Therefore, with filters described above, the majority of these impurities can be removed before the materials are counted and the threshold of the CNC 52 is such that other residue which passes to the CNC 52 will not be counted. Dilution of the sample with solvent also allows the user to ensure a more accurate count.

Because some residue is eliminated prior to the passage of the particles to the CNC 52 and prior to the counting, an accurate measurement of material concentration is possible. Because the volume of the sample is known, the relationship between the volume and the concentration may be utilized to achieve a highly accurate measurement of the number of macromolecules or colloids of the analyte. As discussed above, the rejection of the background heightens accuracy. Further, the CNC 52 detects single particles in real time. The narrowness of the detected light pulse and built-in flow dilution allows for single particle detection.

An alternative embodiment of the present invention includes use of a pneumatic atomizer as shown in FIGS. 3 and 4. A pneumatic atomizer 116 is connected to the chromatography system 112 or syringe pump 114 to receive the liquid sample. The atomizer 116 includes inlet 115, outlet 133 and gas inlet 131. The chromatography apparatus 112 is connected to the atomizer 116 to directly feed the sample to be analyzed thereto. Tubing 113 is utilized to allow the sample to flow to the atomizer 116 through inlet 115. In the preferred embodiment, the atomizer 116 is made from stainless steel material and is manufactured by TSI Incorporated of St. Paul, Minn., having a model designation as Model 3076. The tubing utilized in the preferred embodiment is of stainless steel or PFA material.

Referring to FIG. 4, the atomizer 116 is modified by means of an adjustable rod 117. The rod 117 allows for generation of droplets of a reduced size. The rod 117 includes impaction surface 117*a*. Further modifications include reducing the inlet orifice diameter 131 from the standard model diameter, and placing the impaction surface 117*a* closer to the orifice 131. The rod 117 is shown in FIG. 4 and in the preferred embodiment is generally circular in cross section with a diameter of 0.375 inches. The rod 117 is adjustable so that larger droplets may impact on it, thereby producing uniformly smaller droplets. Larger droplets impact the rod 117 and by gravity fall to a waste reservoir 119 within atomizer 116.

The atomizer 116 is supplied with compressed air at inlet 131 to atomize the liquid. As shown in FIG. 3, the gases are supplied by gas supply 118 connected to the atomizer 116. The gas supply 118 is in fluid communication with the atomizer 116. The atomizer 116 receives the sample to be analyzed and with the compressed air or nitrogen from gas supply 118, atomizes the sample, and generates a mist. The gas supply 118 is regulated by a pressure regulator 121. The gas flows through a filter 120, which is connected upstream from atomizer 116, to screen out impurities. The filter 120 is cooperatively connected to the atomizer 116 to filter the inlet air. This filter is necessary to remove particles which may contribute to the aerosol background which would distort the results. The filter 120 is a pleated glass fiber, high efficiency filter manufactured by TSI Incorporated of St. Paul, Minn., known as Model 3074 in the preferred embodiment.

The mist created by atomizer 116 includes a large number of fine droplets having a predetermined size distribution. Large droplets, that is, particles of several microns, impact the rod surface 117*a* of the atomizer 116 and drain to the bottom of the atomizer device 116 to reservoir 119. These large droplets that drain to the bottom reservoir 119 are collected in the closed reservoir 119 and later removed. The remaining droplets which contain the target macromolecules or colloidal particles exit the atomizer 116 at outlet 133. The droplets flow through connector 135 to drying column 122.

Again referring to FIG. 3, a drying column 122 is utilized in the preferred embodiment to remove the solvent or background from the sample or analyte. In the preferred embodiment, heated compressed air from supply 118 enters a drying column 122 by means of tubing 126. The air evaporates the solvent and leaves the aerosol in the drying column 122. Pressure regulator 121 connected upstream of column 122, regulates the flow of drying air. A fixed orifice 127 connected to tubing 126 downstream of pressure regulator 121 further controls the flow of drying air. In the preferred embodiment, orifice 127 is a critical type orifice. Use of the critical type orifice allows for slow control without the use of the regulating means. The air which enters the drying column 122 is filtered. In the preferred embodiment, filter 129, downstream of orifice 127, filters the drying air to ensure that impurities are not introduced into the system. In the preferred embodiment of the invention described here, a pleated glass high efficiency filter is utilized. Heater 140 is connected to tubing 126 downstream of filter 129. Heater 140 heats the compressed drying air before it flows into drying column 122. The air must be filtered so that no contaminants contribute to the aerosol background or are counted in the measurement of concentration of target colloids or macromolecules.

A sample of aerosol is drawn into connector tubing 128 at the bottom of the drying column 122. In the preferred embodiment, the aerosol is drawn into tube 128 by an internal pump of a condensation nucleus counting device 130. Outlet 136, at the bottom of column 122, provides a means for exhaust of the aerosol not taken into the system at connector tubing 128.

Connector tubing 128 is cooperatively connected, in the preferred embodiment, to the drying column 122 to provide a means for passage of aerosols from the drying column 122 to a means for counting the aerosols or a condensation nucleus counter 130. As previously discussed, the aerosols are received by the condensation nucleus counter or the CNC 130 and serve as nuclei for the condensation of liquid droplets from supersaturated vapor. Thus, the concentration of the separated materials can be measured utilizing the CNC 130.

Diffusion screens 132 may be utilized with this alternative embodiment to shift the detection efficiency curve of the CNC 130 to larger size. A diffusion filter housing 137 may hold the screens 132 as described above.

In yet another alternative embodiment, a desiccant or absorbent agent may be utilized to absorb solvent vapor. The following desiccants may be utilized with the present invention: silica gel, calcium chloride, etc. However, it should be understood that any other suitable means for drying the particles to form an aerosol may be utilized.

While a particular embodiment of the invention has been described with respect to its application in conjunction with chromatography, it should be understood by those skilled in the art that the invention is not limited to such application or embodiment or to the particular components disclosed and described herein. It will be appreciated by those skilled in the art that other configurations that embody the principles of this invention and applications other than described herein can be configured within the spirit and the intent of this invention. The configuration described herein is provided only as an example of one embodiment that incorporates and practices the principles of this invention. Other modifications and alterations well within the knowledge of those skilled in the art are to be included within the broad scope of the appended claims.

Appendix A

Number Concentration and Statistics of Macromolecules or Colloids in Droplets For simplicity, we assume that the droplets formed are monodisperse, having volume V per droplet. Let x be the average number of macromolecules or colloids per droplet. Then $$x = C \cdot V$$

where C is the macromolecule or colloid number concentration. The a priori probability that a given droplet contains exactly n particles is then given by the Poisson formula:

$$P(n:x) = \frac{e^{-x} x^n}{n!}$$

To avoid complex data analysis, we wish to operate the apparatus under conditions such that it is very unlikely for a droplet to contain more than one macromolecule or colloid. We can calculate the probability that a given droplet contains two or more macromolecules or colloids by the following formula:

$$P(n>1:x) = 1 - P(o:x) - P(1:x)$$

which, using the Poisson expression, is $$P(n>1:x) = 1 - e^{-x}(1+x)$$

Figure 6:
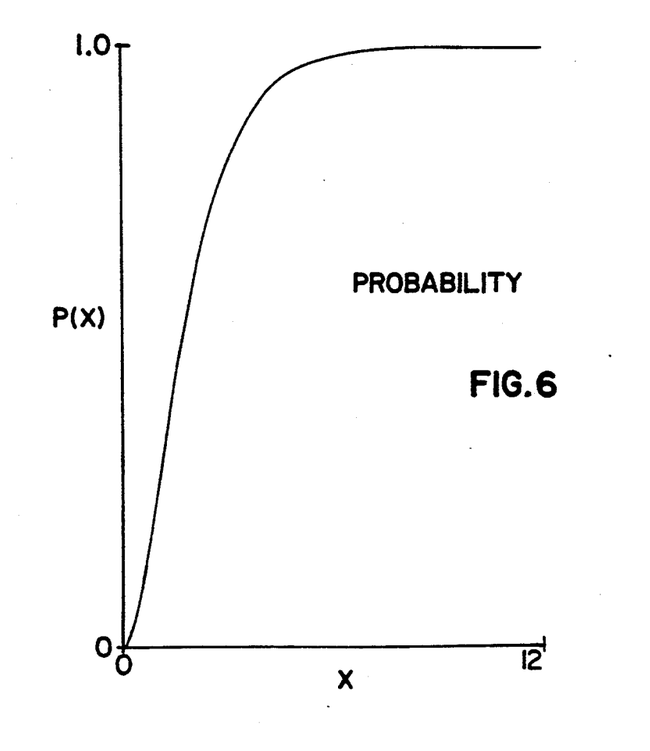
FIG. 6 is a graph illustrating the Poisson expression described in Appendix A.

This function is plotted in FIG. 6.

The above results show that to keep the probability of having more than one particle per droplet less than 1%, it is sufficient to keep x less than 0.1. Assuming a mean droplet volume $V = 1.42 \times 10^{-14}$ milliliter, corresponding to a droplet diameter of 0.3 micrometers, and $x = 0.1$, concentration of $7 \times 10^{-12}$ P/ml (particle/ml) is obtained. Sample concentration less than $7 \times 10^{-12}$ P/ml keeps the probability of having more than one particle per droplet even less than 1%.

We claim:

1. A device for determining the concentration of macromolecules and colloids in a liquid of the type that can include the macromolecules, colloids, and impurities, said device comprising:

(a) means for forming droplets from the liquid;

(b) means, cooperatively connected to said droplet forming means, for removing the liquid from the droplets wherein an aerosol results;

(c) means, cooperatively connected to said liquid removing means, for selecting aerosol particles of a size greater than a predetermined size; and (d) means for counting the aerosol particles greater than the predetermined size.

2. The device of claim 1 wherein said means for forming droplets includes an electrospray device.

3. The device of claim 1 wherein said means for forming droplets includes a pneumatic atomizer.

4. The device of claim 2 further comprising means for neutralizing the particle cooperatively connected to said liquid removing means.

5. The device of claim 3 further comprising means for neutralizing the aerosol.

6. The device of claim 1 wherein said means for selecting the aerosols of a size greater than a predetermined size further includes a variable number of diffusion screens, said diffusion screens operatively connected to said counting means.

7. The device of claim 1 wherein said liquid removing means includes a source of heated air.

8. The device of claim 1 wherein said liquid removing means includes a desiccant.

9. The device of claim 1 wherein said means for counting includes a condensation nucleus counter.

10. The device of claim 1 wherein said means for counting includes an optical particle counter.

11. A device for detecting macromolecules and colloids in a liquid of the type that can include the macromolecules, colloids and impurities, said device comprising:

(a) a chamber;

(b) means for forming charged droplets from the liquid;

(c) means for removing the liquid from the droplets within said chamber wherein an aerosol results;

(d) means cooperatively connected to said liquid removing means, for selecting aerosol of a size greater than a predetermined size;

(e) means located within said chamber sequentially downstream of said droplet forming means, for neutralizing the charged aerosols; and (f) means operatively connected to said chamber for counting the aerosols.

12. The device of claim 11 wherein said means for forming charged droplets includes an electrospray device.

13. The device of claim 11 wherein said liquid removing means includes a source of heated air.

14. The device of claim 11 wherein said liquid removing means includes a desiccant.

15. The device of claim 11 wherein said neutralizing means includes an α-particle source.

16. The device of claim 11 wherein said counting means includes a condensation nucleus counter.

17. The device of claim 16 further including a variable number of diffusion screens, said diffusion screens operatively connected to said condensation nucleus counter for altering the operating range of the device.

18. An apparatus for determining the concentration of macromolecules and colloids in a liquid of the type that can include the macromolecules, colloids and impurities, said device comprising:

(a) means for separating the liquid sample into its components according to a desired physical property;
(b) means for forming charged droplets from the liquid;
(c) delivery means, cooperatively connected to said separating means, for placing the liquid in communication with said droplet forming means;
(d) means for removing the liquid from the droplets wherein the charged aerosols result;
(e) means for neutralizing the charged aerosols located sequentially downstream said means for forming charged droplets;
(f) means for selecting the macromolecules and colloids for counting; and (g) means for counting the macromolecules and colloids.

19. An apparatus for determining the concentration of macromolecules and colloids in a liquid of the type that can include the macromolecules, colloids, and impurities, said device comprising:

(a) means for separating the liquid according to a desired physical property;

(b) means for forming droplets from the liquid;

(c) delivery means, cooperatively connected to said separating means, for placing the liquid in communication with said droplet forming means;

(d) means for removing the liquid from the droplets wherein the aerosols result;

(e) means for selecting the macromolecules and colloids for counting; and (f) means for counting the macromolecules and colloids.

20. The apparatus of claim 19 wherein said means for separating the sample includes a liquid chromatograph.

21. An apparatus for measuring the concentration of macromolecules and colloids in a liquid of the type that can include the macromolecules, colloids and impurities, said device comprising:

(a) a liquid chromatograph for separating the liquid according to a desired physical property;

(b) a chamber, said chamber having an entrance and an exit and having a generally cylindrical shape;

(c) means for forming charged droplets from the liquid within said chamber, said means for forming charged droplets including an atomizer;

(d) delivery means, cooperatively connected to said liquid chromatograph for placing the liquid in fluid communication with said droplet forming means at said chamber entrance;

(e) a desiccant for absorbing the liquid vapor;

(f) an $\alpha$-particle source located within said chamber sequentially downstream of said droplet forming means for neutralizing the charged aerosols; and (g) a condensation nucleus counter cooperatively connected to said chamber exit for counting said macromolecules and colloids.

22. A method for determining the concentration of macromolecules and colloids in a liquid of the type that can include the macromolecules, colloids and impurities, said method comprising the steps of:

(a) forming droplets from the liquid;

(b) removing the liquid from the droplets, wherein an aerosol results;

(c) selecting the aerosols of a size greater than a predetermined size; and (d) counting the macromolecules and colloids.

* * * * *